US005508276A

United States Patent [19]

Anderson et al.

[11] Patent Number: 5,508,276

[45] Date of Patent: Apr. 16, 1996

[54] DULOXETINE ENTERIC PELLETS

[75] Inventors: Neil R. Anderson, West Lafayette; Peter L. Oren, Fishers, both of Ind.; Toshihiro Ogura, Osaka; Toshiro Fujii, Hyogo, both of Japan

[73] Assignees: Eli Lilly and Company, Indianapolis, Ind.; Shionogi & Co., Osaka, Japan

[21] Appl. No.: 276,232

[22] Filed: Jul. 18, 1994

[51] Int. Cl.[6] .................................................. A01N 43/00

[52] U.S. Cl. .......................... 514/183; 424/458; 424/459; 424/461; 424/463; 424/464

[58] Field of Search ............................ 514/183; 424/458, 424/459, 461, 463, 464

[56] References Cited

U.S. PATENT DOCUMENTS

| | | | |
|---|---|---|---|
| 4,017,647 | 4/1977 | Ohno et al. . | |
| 4,853,230 | 8/1989 | Lovgren et al. . | |
| 5,362,886 | 11/1994 | Berglund | 549/75 |

FOREIGN PATENT DOCUMENTS

| | | |
|---|---|---|
| 2057876 | 8/1980 | United Kingdom . |

OTHER PUBLICATIONS

Delattre, et al., *Proceed. Intern. Symp. Control. Rel. Bioact. Mater.*, 19, 267–268 (1992).

Osterwald, *Pharmaceutical Research*, 14–18 (1985).

Chang, *Pharmaceutical Technology*, 62–70 (Oct. 1990).

Stafford, *Drug Development & Industrial Pharmacy*, 8(4), 513–530 (1982).

Bloor, et al., *Drug Development & Industrial Pharmacy*, 15(14–16), 2227–2243 (1989).

Davis, et al., *Drug Development & Industrial Pharmacy*, 12(10), 1419–1448 (1986).

Schmidt and Niemann, *Drug Development & Industrial Pharmacy*, 18(18), 1969–1979 (1992).

Nagai, et al., *Aqueous Polymeric Coatings for Pharmaceutical Dosage Forms*, Marcel Dekker, N.Y. and Basel, 81–152 (1989).

Wyatt, "Enhanced Stability of Aqueous Cellulose Acetate Phthalete (C–A–P) Enteric Films", presented 7th Ann. AAPS Conf., San Antonio, Tex., Nov. 15–19, 1992.

Fujii, et al., *Pre–World Congress Particle Technology in Gifu*, Sep. 17–18, 1990, Gifu, Japan, 80–85.

Yakuji Nippo. Ltd., *Japanese Standards of Pharmaceutical Ingredients*, 1216–1221 (1991).

Shin–Etsu Chemical Co., Ltd., "An Improved Aqueous Coating Using Shin–Etsu Aqoat", *Technical Information Bulletin* (1994).

*Primary Examiner*—Nathan M. Nutter

*Attorney, Agent, or Firm*—Joseph A. Jones; David E. Boone

[57] ABSTRACT

A superior enteric formulation of the antidepressant drug, duloxetine, is in the form of enteric pellets of which the enteric layer comprises hydroxypropylmethylcellulose acetate succinate.

18 Claims, No Drawings

DULOXETINE ENTERIC PELLETS

FIELD OF THE INVENTION

This invention belongs to the field of pharmaceutical science, and provides a superior enteric formulation of the anti-depressant drug, duloxetine.

BACKGROUND OF THE INVENTION

Duloxetine is now in clinical research as a candidate anti-depressant. See, for example, Wong et al., *Neuropsychopharmacology,* 8, 23–33 (1993), where the compound is named by its research number LY248686. Duloxetine is (+)-N-methyl-3-(1-naphthalenyloxy)-2-thiophenepropanamine, and is commonly used as its hydrochloride salt. In this document, the word "duloxetine" will refer to the hydrochloride salt of the specific enantiomer just named.

Enteric pharmaceutical formulations are manufactured in such a way that the product passes unchanged through the stomach of the patient, and dissolves and releases the active ingredient quickly when it leaves the stomach and enters the small intestine. Such formations have long been used, and conventionally are in tablet or pellet form, where the active ingredient is in the inner part of the tablet or pellet and is enclosed in a film or envelope, the "enteric coating", which is insoluble in acid environments, such as the stomach, but is soluble in near-neutral environments such as the small intestine.

Early dosage form and clinical development of duloxetine showed that it is advisable to formulate it in an enteric form, due to the stability characteristics of duloxetine in acidic solutions, that a pellet formulation was more desirable than a tablet, based on bioavailability studies which showed more consistent plasma profiles were obtained after pellet administration, and that certain difficulties arose in preparing conventional enteric formulations.

Most importantly, duloxetine was found to react with many enteric coatings to form a slowly- or even insoluble coating. Because of this unexpected cross-reactivity, formulations in pellet form were found to have a disadvantageous drug-releasing profile and low bioavailability.

Further, it was found to be particularly difficult to prepare an enteric formulation with higher levels of drug loading which did not allow some release of duloxetine in acid environments, thus creating a possibility or probability that drug would be released in the stomach, contrary to the desired method of administration.

The present invention was created through efforts to solve the above and other problems, and provides a superior enteric formulation of duloxetine.

SUMMARY OF THE INVENTION

The present invention provides an enteric duloxetine pellet comprising a) a core consisting of duloxetine and a pharmaceutically acceptable excipient; b) an optional separating layer; c) an enteric layer comprising hydroxypropylmethylcellulose acetate succinate (HPMCAS) and a pharmaceutically acceptable excipient; d) an optional finishing layer.

The invention also provides a method of manufacturing an enteric duloxetine pellet comprising a) providing a core consisting of duloxetine and a pharmaceutically acceptable excipient; b) optionally, applying to the core a separating layer comprising a pharmaceutically acceptable excipient; c) applying an enteric layer comprising HPMCAS and a pharmaceutically acceptable excipient, wherein the HPMCAS is applied as an aqueous solution or suspension and the application takes place in an apparatus of the fluid bed type; d) optionally, applying a finishing layer.

DETAILED DESCRIPTION AND PREFERRED EMBODIMENTS

Throughout the present document, all expressions of percentage, ratio, proportion and the like, will be in weight units unless otherwise stated. Expressions of proportions of the enteric product will refer to the product in dried form, after the removal of the water in which many of the ingredients are dissolved or dispersed.

The various components and layers of the pellet will be individually discussed as follows, together with the methods of adding the different ingredients to build up the duloxetine pellet.

The Core

A preferred core for the pellet is prepared by applying a duloxetine-containing layer to an inert bead. Such inert beads are conventionally used in pharmaceutical science, and are readily purchased in all industrial countries. The most preferred bead is one prepared from starch and sucrose, for use in confectionery as well as in pharmaceutical manufacturing. However, beads of any pharmaceutically acceptable excipient may be used, including, for example, microcrystalline cellulose, vegetable gums, waxes, and the like. The primary characteristic of the inert bead is to be inert, with regard both to duloxetine and the other excipients in the pellet and with regard to the patient who will ultimately ingest the pellet.

The size of the beads depends, of course, on the desired size of the pellet to be manufactured. In general, pellets can be as small as 0.1 mm, or as large as 2 mm. Preferred beads are from about 0.3 to about 0.8 mm, in order to provide finished pellets in the desired preferred size range of from about 0.5 to about 1.5 mm in diameter.

It is always preferred for the beads to be of a reasonably narrow particle size distribution, in order to improve the uniformity of the various coatings to be added and the homogeneity of the final product. For example, the beads may be specified as being of particle size ranges such as from 18 to 20 U.S. mesh, from 20 to 25 U.S. mesh, or from 25 to 35 U.S. mesh to obtain acceptable size distributions of various absolute sizes.

The amount of beads to be used obviously depends on the weights and thicknesses of the added layers; in general, the beads comprise from about 15 to about 70 percent of the product. More preferably, the charge of beads represents from about 20 to about 65 percent of the product.

When manufacture of the pellet begins with inert beads, the duloxetine is coated on the beads to yield a final drug concentration of about 1 to about 15 percent of the product, in general. The amount of duloxetine, of course, depends on the desired dose of the drug and the quantity of pellets which it is desired to administer. The dose of duloxetine is in the range of 1–50 mg, more usually 5–20 mg, and the usual amount of pellets is that amount which is conveniently held in gelatin capsules. Comparison of the volume of gelatin capsules and the desired doses leads the pharmacist to the concentration range of from about 1% to about 15% of duloxetine in the present product.

Some attention must be given to the particle size of duloxetine. The compound can precipitate in needle-like crystals which can be quite large. Coating beads with duloxetine in the large needle-like form can be difficult, and it is advisable to mill or otherwise reduce the particle size of the duloxetine to less than about 50 μm before using it in the present product and process.

A convenient manner of coating the beads with duloxetine is the "powder coating" process where the beads are moistened with a sticky liquid or binder, duloxetine is added as a powder, and the mixture is dried. Such a process is regularly carried out in the practice of industrial pharmacy, and suitable equipment is in daily use.

Such equipment is, in fact, used in several steps of the present process, and it will, accordingly, be discussed in detail here. Historically, this process has been conducted in conventional coating pans similar to those employed in sugar coating processes. This process can be used to prepare pellets, but this equipment has less efficient air flow and drying capabilities which limits application rates and can result in longer processing times in order to minimize agglomerations.

Alternately, the present product could be made in fluidized bed equipment (using a rotary processor), or in rotating plate equipment such as the Freund CF-Granulator (Vector Corporation, Marion, Iowa). The rotating plate equipment typically consists of a cylinder, the bottom of which is a rotatable plate. Motion of the mass of particles to be coated is provided by friction of the mass between the stationary wall of the cylinder and the rotating bottom of it. Means can be provided to apply warm air to dry the mass, and liquids can be sprayed on the mass and balanced against the drying rate as in the fluidized bed case.

When a powder coating is to be applied, the mass of pellets, in the present case, is maintained in a sticky state, and the powder to be adhered to them, duloxetine in this case, is added continuously or periodically and adheres to the sticky pellets. When all of the duloxetine has been applied, the spray is stopped and the mass is allowed to dry in the air stream. It may be appropriate or convenient to add some inert powders to the duloxetine.

Additional solids may be added to the layer with duloxetine. These solids may be added to facilitate the coating process as needed to aid flow, reduce static charge, aid bulk buildup and form a smooth surface. Inert substances such as talc, kaolin, and titanium dioxide, lubricants such as magnesium stearate, finely divided silicon dioxide, crospovidone, and β-lactose may be used. The amounts of such substances are in the range from about a few tenths of 1% of the product, up to about 20% of the product. Such solids should be of fine particle size, less than 50 μm, to produce a smooth surface.

The duloxetine is made to adhere to the beads by spraying a pharmaceutical excipient which is sticky and adherent when it is wet, and dries to a strong, coherent film. Pharmaceutical scientists are aware of and conventionally use many such substances, most of them polymers. Preferred such polymers include hydroxypropylmethylcellulose, hydroxypropylcellulose and polyvinylpyrrolidone. Additional such substances include methylcellulose, carboxymethylcellulose, acacia and gelatin, for example. The amount of the adhering excipient is in the range from about a few tenths of 1% to about 5% of the product, and depends in large part on the amount of duloxetine to be adhered to the bead.

Duloxetine may also be built up on the beads by spraying a slurry comprising duloxetine suspended in a solution of the excipients of the duloxetine layer, dissolved or suspended in sufficient water to make the slurry sprayable. Such a slurry may be milled through a machine adapted for grinding suspensions in order to reduce the particle size of duloxetine. Grinding in suspension form is desirable because it avoids dust generation and containment problems which arise in grinding dry powder drugs. A preferred method for applying this suspension is in the classic pharmaceutical fluidized bed coating device, such as the Wurster column, which consists simply of a vertical cylinder with an air-permeable bottom and an upward spraying nozzle close above the bottom, or a downward-spraying nozzle mounted above the product mass. The cylinder is charged with particles to be coated, sufficient volume of air is drawn through the bottom of the cylinder to suspend the mass of particles, and the liquid to be applied is sprayed onto the mass. The temperature of the fluidizing air is balanced against the spray rate to maintain the mass of pellets or tablets at the desired level of moisture and stickiness while the coating is built up.

On the other hand, the core may comprise a monolithic particle in which the duloxetine is incorporated. Such cores may be prepared by the granulation techniques which are wide spread in pharmaceutical science, particularly in the preparation of granular material for compressed tablets. The particle size of the cores is too small for preparation by compression techniques, but the cores may be prepared by mixing the duloxetine into a mass of pharmaceutical excipients, moistening the mass with water or a solvent, drying, and breaking the mass into sized particles in the same size range as described above for the inert beads. This can be accomplished via the process of extrusion and marumerization.

The core for the pellet can also be prepared by mixing duloxetine with conventional pharmaceutical ingredients to obtain the desired concentration and forming the mixture into cores of the desired size by conventional procedures or by the process of R. E. Sparks, et al., U.S. Pat. Nos. 5,019,302 and 5,100,592, incorporated by reference herein.

Separating Layer

The separating layer between the duloxetine-containing core and the enteric layer is not required, but is a preferred feature of the formulation. The functions of the separating layer, if required, are to provide a smooth base for the application of the enteric layer, to prolong the pellet's resistance to acid conditions, to improve stability by inhibiting any interaction between the drug and the enteric polymer in the enteric layer, and to improve stability by protecting the drug from light exposure.

The smoothing function of the separating layer is purely mechanical, the objective of which is to improve the coverage of the enteric layer and to avoid thin spots in it, caused by bumps and irregularities on the core. Accordingly, the more smooth and free of irregularities the core can be made, the less material is needed in the separating layer, and the need for the smoothing characteristic of the separating layer may be avoided entirely when the duloxetine is of extremely fine particle size and the core is made as close as possible to truly spherical.

It has been found that, when a pharmaceutically acceptable sugar is added to the separating layer, the pellet's resistance to acid conditions is markedly and surprisingly increased. Accordingly, such a sugar may be included in the separating layer applied to the beads, either as a powdered mixture, or dissolved as part of the sprayed-on liquid. A sugar-containing separating layer can reduce the quantity of enteric polymer required to obtain a given level of acid resistance. It therefore considerably reduces the expense of the present formulated product. Use of less enteric polymer reduces both the materials cost and processing time, and also reduces the amount of polymer available to react with duloxetine. The inhibition of any core/enteric layer interaction is mechanical. The separating layer physically keeps the components in the core and enteric layers from coming into direct contact with each other. In some cases, the separating layer can also act as a diffusional barrier to migrating core or enteric layer components dissolved in product moisture. The separating layer can also be used as a light barrier by opacifying it with agents such as titanium dioxide, iron oxides and the like.

In general, the separating layer is composed of coherent or polymeric materials, and finely powdered solid excipients which constitute fillers. When a sugar is used in the separating layer, it is applied in the form of an aqueous solution and constitutes part of or the whole of the coherent material which sticks the separating layer together. In addition to or instead of the sugar, a polymeric material may also be used in the separating layer. For example, substances such as hydroxypropylmethylcellulose, polyvinylpyrrolidone, hydroxypropylcellulose and the like may be used in small amounts to increase the adherence and coherence of the separating layer.

It is further advisable to use a filler excipient in the separating layer to increase the smoothness and solidity of the layer. Substances such as finely powdered talc, silicon dioxide and the like are universally accepted as pharmaceutical excipients and may be added as is convenient in the circumstances to fill and smooth the separating layer.

In general, the amount of sugar in the separating layer may be in the range of from about 2% to about 10% of the product, when a sugar is used at all, and the amount of polymeric or other sticky material may be in the range of from about 0.1 to about 5%. The amount of filler, such as talc, should be in the range of from about 5 to about 15%, based on final product weight.

The separating layer may be applied by spraying aqueous solutions of the sugar or polymeric material, and dusting in the filler as has been described in the preparation of a duloxetine layer. The smoothness and homogeneity of the separating layer can be improved, however, if the filler is thoroughly dispersed as a suspension in the solution of sugar and/or polymeric material, and the suspension is sprayed on the core and dried, using equipment as described above in the preparation of cores with duloxetine layers.

Enteric Layer

The enteric layer is comprised of an enteric polymer, which must be chosen for compatibility with duloxetine as discussed above. The polymer must be one having only a small number of carboxylic acid groups per unit weight or repeating unit of the polymer. The preferred enteric polymer is hydroxypropylmethylcellulose acetate succinate (HPMCAS), which product is defined as containing not less than 4% and not more than 28% of succinoyl groups, which are the only free carboxylic groups in the compound. See Japanese Standards of Pharmaceutical Ingredients 1991, page 1216–21, Standard No. 19026. HPMCAS is available from Shin-Etsu Chemical Co., Ltd., Tokyo, Japan, under the trademark AQOAT. It is available in two particle size grades and three molecular weight ranges. The L grade, having number average molecular weight of 93,000, is used in the present examples but other grades are expected to be usable.

Enteric polymers may be applied as coatings from aqueous suspensions or from solutions in aqueous or organic solvents. Application from organic solvents is presently not at all favored in the pharmaceutical industry, because of the cost of the solvent and the difficulty in either disposing of solvent vapors or recovering the evaporated solvent. Accordingly, no detailed discussion of application of the enteric layer from organic solvents will be given here, but the pharmaceutical scientist will recognize that such application is entirely possible if circumstances favor it.

When the enteric polymer is applied as an aqueous suspension, a problem in obtaining a uniform, coherent film often results. It is very advisable, accordingly, to purchase a fine particle grade or grind the particles of polymer to an extremely small size before application. It is possible either to grind the dry polymer, as in an air-impaction mill or to prepare the suspension and grind the polymer in slurry form. Slurry grinding is generally preferable, particularly since it can be used also to grind the filler portion of the enteric layer in the same step. It is advisable to reduce the average particle size of the enteric polymer to the range from about 1 μm to about 5 μm, preferably no larger than 3 μm.

When the enteric polymer is applied in the form of a suspension, it is important to assure that the suspension remains homogeneous, and that conditions which favor the agglomeration of the polymer do not occur. Such precautions include maintaining the suspension in a gently stirred condition, but not stirring so vigorously as to create foam, and assuring that the suspension does not stand still in eddies in nozzle bodies, for example, or in over-large delivery tubing. Frequently polymers in suspension form will agglomerate if the suspension becomes too warm, and the critical temperature may be as low as 30° C. in individual cases. Since spray nozzles and tubing are exposed to hot air in the usual fluid bed type equipment, care must be taken to assure that the suspension is kept moving briskly through the equipment to cool the tubing and nozzle. When HPMCAS is used, in particular, it is advisable to cool the suspension below 20° C. before application, to cool the tubing and nozzle by pumping a little cold water through them before beginning to pump the suspension, and to use supply tubing with as small a diameter as the spray rate will allow so that the suspension can be kept moving rapidly in the tubing.

It is preferred in the present invention, however, to apply the enteric polymer as an aqueous solution whenever it is possible to do so. In the case of HPMCAS, dissolution of the polymer can be obtained by neutralizing the polymer, preferably with ammonia. Neutralization of the polymer may be obtained merely by adding ammonia, preferably in the form of aqueous ammonium hydroxide to a suspension of the polymer in water; complete neutralization results in complete dissolution of the polymer at about pH 5.7–5.9. Good results are also obtained when the polymer is partially neutralized, by adding less than the equivalent amount of ammonia. In such case, the polymer which has not been neutralized remains in suspended form, suspended in a solution of neutralized polymer. As noted earlier, it is obviously important to control the particle size of the polymer when such a process is to be used. Use of neutralized polymer more readily provides a smooth, coherent enteric layer than when a suspended polymer is used, and use of partially neutralized polymer provides intermediate degrees of smoothness and coherency. Particularly when the enteric layer is applied over a very smooth separating layer, excellent results may be obtained from partially neutralized enteric polymer.

The extent of neutralization may be varied over a range without adversely affecting results or ease of operation. For example, operation with from about 25% to about 100% neutralization is preferred in the present invention. Another preferred condition is from about 45% to about 100% neutralization, and another preferred condition is from about 65% to about 100%. Still another preferred manner of neutralization is from about 25% to about 65% neutralized. It is found, however, that the enteric polymer in the resulting product, after drying, is neutralized to a lesser extent than when applied. When neutralized or partially neutralized HPMCAS is applied, the HPMCAS in the final product is from about 0% to about 25% neutralized, more preferably from about 0% to about 15% neutralized.

Most enteric polymers require the addition of a plasticizer for best results. In the case of HPMCAS, the preferred plasticizer is triethyl citrate, used in an amount up to about 15%–30% of the amount of enteric polymer in aqueous suspension application. When a neutralized HPMCAS is employed, lower levels or no plasticizer may be required.

Minor ingredients, such as antifoam, suspending agents when the polymer is in suspended form, and surfactants to assist in smoothing the film are also commonly used. For example, silicone anti-foams, surfactants such as polysorbate 80, sodium lauryl sulfate and the like and suspending agents such as carboxymethylcellulose vegetable gums and the like may commonly be used at amounts in the general range up to 1% of the product.

Usually, an enteric layer is filled with a powdered excipient such as talc or hydrated silicon dioxide to build up the thickness of the layer, to strengthen it, to reduce static charge, and to reduce particle cohesion. Amounts of such solids in the range of from about 5% to about 30% of the final product may be added to the enteric polymer mixture, while the amount of enteric polymer itself is usually in the range from about 10% to about 30%, more preferably, from about 15% to about 25%.

Application of the enteric layer to the pellets follows the same general procedure previously discussed, using fluid bed type equipment with simultaneous spraying of enteric polymer solution or suspension and warm air drying. Temperature of the drying air and the temperature of the circulating mass of pellets should be kept in the ranges advised by the manufacturer of the enteric polymer.

It is also possible to include an opacifying agent in the enteric layer, in the present case, to protect the duloxetine from light. The most efficient and commonly used opacifiers in pharmaceutical science are the finely powdered oxides of titanium and iron. Amounts of opacifier in the range up to as much as 15% of the product weight, preferably in the range from about 2% to about 10%, will certainly increase the pharmaceutical elegance of the pellets and are likely to improve further the product's stability.

Finishing Layer

A finishing layer over the enteric layer is not necessary in every case, but frequently improves the elegance of the product and its handling, storage and machinability and may provide further benefits as well. The simplest finishing layer is simply a small amount, about less than 1% of an anti-static ingredient such as talc or silicon dioxide, simply dusted on the surface of the pellets. Another simple finishing layer is a small amount, about 1%, of a wax such as beeswax melted onto the circulating mass of pellets to further smooth the pellets, reduce static charge, prevent any tendency for pellets to stick together, and increase the hydrophobicity of the surface.

More complex finishing layers may constitute a final sprayed-on layer of ingredients. For example, a thin layer of polymeric material such as hydroxypropylmethylcellulose, polyvinylpyrrolidone and the like, in an amount such as from a few tenths of 1% up to about 3%, may be applied. The polymeric material may also carry a suspension of an opacifier, a bulking agent such as talc, or a coloring material, particularly an opaque finely divided color agent such as red or yellow iron oxide. Such a layer quickly dissolves away in the stomach, leaving the enteric layer to protect the duloxetine, but provides an added measure of pharmaceutical elegance and protection from mechanical damage to the product.

Finishing layers to be applied to the present product are of essentially the same types commonly used in pharmaceutical science to smooth, seal and color enteric products, and may be formulated and applied in the usual manners.

The following Examples set out the preparation of a number of different enteric granules within the concept of the present invention. The Examples are intended further to enlighten the reader about the present enteric granules and their methods of manufacture; additional variations within the concept of the invention will be clear to the pharmaceutical scientist and their preparation will be within the scientist's competence.

For each example, a bill of materials will first be given, which will be expressed in terms of the amount of each ingredient used to prepare a single unit dose of the granules. Following the bill of materials, the process will be described, giving the equipment and the batch size used in the various stages of manufacture.

EXAMPLE 1

10 mg Duloxetine base/capsule

| Bill of Materials | |
|---|---|
| Beads | |
| Microcrystalline cellulose, 32–42 mesh | 30.00 mg |
| Duloxetine layer | |
| Duloxetine | 11.23 |
| β-lactose | 48.77 |
| Cross-linked polyvinylpyrrolidone (crospovidone) | 6.00 |
| Hydroxypropylcellulose | 0.72 |
| Talc | 8.00 |
| Separating layer | |
| Hydroxypropylmethylcellulose | 1.20 |
| Polyethylene glycol 6000 | 4.60 |
| Talc | 13.90 |
| Titanium dioxide | 1.20 |
| Enteric layer | |
| HPMCAS-LF, Shin-Etsu, 5 μm average particle size | 44.70 |
| Triethyl citrate | 10.70 |
| Talc | 13.40 |
| Finishing layer | |
| White beeswax | 1.90 |
| Hydrated silicon dioxide | 0.40 |
| | 196.72mg. |

The duloxetine layer was added to the beads in a CF granulator at a batch size of 3.6 kg. The hydroxypropylcellulose was dissolved in a minimum amount of water, and the solution was slowly sprayed onto the agitating batch of beads, while the duloxetine, lactose and crospovidone, as a mixture was intermittently added at a rate such that it would be adhered to the beads without loss through dusting. When the duloxetine layer was fully formed, the talc was added in the same manner, and the beads were dried in an oven at 55° C. for 1.5 hours, and then classified between 20 and 42 mesh screens.

Then the separating layer was applied in a Wurster column (Uni-Glatt, Glatt Air Techniques, Inc., Ramsey, N.J.). The hydroxypropylmethylcellulose and the polyethylene glycol were dissolved in water, and the talc and titanium dioxide were dispersed in the solution with a homogenizer. The resulting suspension was sprayed onto the classified beads in the Wurster column.

The enteric coating suspension was prepared by first dissolving the triethyl citrate in water, cooling the solution to 15° C., and preparing a 7% w/v suspension of the HPMCAS-LF in the cool solution. The HPMCAS-LF and talc were added slowly, taking care to avoid foaming or the formation of aggregates of polymer. Then the partially formed granules were added to a fluidized bed coating device, provided with a Wurster column. The batch was fluidized with air at 70°–80° C. and the enteric suspension was sprayed into the batch, taking care that the temperature of the liquid did not rise about 25° C. and adjusting the spray rate and air flow to provide appropriate agitation and avoid agglomeration. When the addition was complete, air flow was continued for 30 minutes to dry the batch.

Finally, the finishing layer was created by adding the beeswax to the product in the fluidized bed at 60° C. After cooling, the hydrated silicon dioxide was added to the pellets and mixed in the Wurster column. The batch was then cooled and filled into number #3 gelatin capsules.

EXAMPLE 2

10 mg Duloxetine base/capsule

| Bill of Materials | | |
|---|---|---|
| Beads | | |
| Microcrystalline cellulose, 32–42 mesh | 30.00 | mg |
| Duloxetine layer | | |
| Duloxetine | 11.23 | |
| B-lactose, 5 μm particle size | 41.27 | |
| Cross-linked polyvinylpyrrolidone | 6.00 | |
| Magnesium stearate | 1.20 | |
| Colloidal silicon dioxide | 0.30 | |
| Talc | 1.50 | |
| Hydroxypropylcellulose | 0.62 | |
| Separating layer | | |
| Talc | 18.50 | |
| Hydroxypropylcellulose | 0.16 | |
| Enteric layer | | |
| HPMCAS-LF, 3 μm particle size | 34.30 | |
| Sorbitan sesquioleate | 0.0002 | |
| Triethyl citrate | 6.90 | |
| Talc | 10.30 | |
| Finishing layer | | |
| Titanium dioxide | 8.66 | |
| Talc | 4.33 | |
| Hydroxypropylmethylcellulose | 3.25 | |
| | 179.42mg. | |

The product was made in substantially the same manner as was the product of Example 1. The duloxetine layer was added in a CF granulator, at a batch size of 5.5 kg. All of the ingredients of the duloxetine layer except the duloxetine, the lactose and the talc were dissolved or suspended in water, and the liquid was slowly sprayed onto the circulating beads and used to adhere the duloxetine, lactose and talc in building up the duloxetine layer.

Similarly, the separating layer was built up in the CF granulator by dissolving the hydroxypropylcellulose in water, and using the solution to adhere the talc on top of the duloxetine layer.

The enteric layer was built up in a fluidized bed granulator provided with a top-spray system at a batch size of 1.3 kg. The sesquioleate was dissolved along with the triethyl citrate in water, following the practice shown in Example 1, and the micronized HPMCAS-LF was carefully dispersed and suspended in the cooled solution for spraying into the fluidized bed, maintaining the temperature of the liquid below 15° C. The temperature of the fluidizing air was 70°–80° C. When the HPMCAS-LF suspension and the talc had been completely added, the batch was dried, and the finishing layer was added in the fluidized bed granulator as well. All of the ingredients of the finishing layer were dissolved or suspended in water, and the suspension was sprayed into the batch, maintaining the fluidized air at 70°–80° C.

Finally, the batch was filled into #3 gelatin capsules.

EXAMPLE 3

10 mg Duloxetine base/capsule

| Bill of Materials | |
|---|---|
| Beads | |
| Sucrose—starch nonpareils, 24–32 mesh | 50.00 mg |
| Duloxetine layer | |
| Duloxetine | 11.23 |
| β-lactose | 47.77 |
| Cross-linked polyvinylpyrrolidone | 7.00 |
| Polyvinylpyrrolidone | 0.53 |
| Separating layer | |
| Hydroxypropylcellulose | 7.00 |
| Talc | 14.00 |
| Enteric layer | |
| HPMCAS-LS, Shin-Etsu, 3 μm average particle size | 31.70 |
| Triethyl citrate | 6.60 |
| Talc | 4.70 |
| Titanium dioxide | 4.70 |
| Sodium dodecylbenzenesulfonate | 0.30 |
| Finishing layer | |
| Titanium dioxide | 4.20 |
| β-lactose | 4.20 |
| Hydroxypropylmethylcellulose | 2.40 |
| Powder layer | |
| Talc | 0.50 |
| | 196.83mg. |

The product was made in a CF granulator, following essentially the same process as described above in Example 1. The powder layer was applied after the product was dried, in a simple rotating pan without air flow. Each dose of completed granules was filled in #3 gelatin capsules.

EXAMPLE 4

10 mg Duloxetine base/capsule

| Bill of Materials | |
|---|---|
| Beads | |
| Sucrose—starch nonpareils 24–32 mesh | 50.00 mg |
| Duloxetine layer | |
| Duloxetine | 11.23 |
| β-lactose | 44.77 |
| Cross-linked polyvinylpyrrolidone | 7.00 |
| Polyvinylpyrrolidone | 0.56 |
| Talc | 3.00 |
| Separating layer | |
| Polyvinylpyrrolidone | 2.44 |
| Talc | 18.00 |
| Enteric layer | |
| HPMCAS-LS, 3 μm particle size | 30.70 |
| Triethyl citrate | 6.40 |
| Sodium dodecylbenzenesulfonate | 0.30 |
| Talc | 4.60 |
| Titanium dioxide | 4.60 |
| Finishing layer | |
| Titanium dioxide | 1.0 |
| β-lactose | 3.80 |
| Hydroxypropylmethylcellulose | 3.80 |
| Powder layer | |
| Talc | 0.50 |
| | 192.80mg. |

The product was made in substantially the same manner as Example 3 above.

EXAMPLE 5

10 mg Duloxetine base/capsule

| Bill of Materials | |
|---|---|
| Beads | |
| Sucrose—starch nonpareils, 20–25 mesh | 107.66 mg |
| Duloxetine layer | |
| Duloxetine | 11.23 |
| Hydroxypropylmethylcellulose | 3.74 |
| Separating layer | |
| Hydroxypropylmethylcellulose | 2.37 |
| Enteric layer | |
| HPMCAS-LF | 23.60 |
| Triethyl citrate | 4.72 |
| Talc 500 mesh | 7.09 |
| | 160.74mg. |

The product was made in a CF* granulator at a batch size of 1.0 kg. The duloxetine layer was built up by spraying into the granulator with inlet air temperature of 80° C. a suspension of the duloxetine in a 120 mg/gm aqueous solution of hydroxypropyl-methylcellulose. The suspension was applied to the slowly, keeping the inlet temperature of the fluidizing air at about 80° C. When the duloxetine suspension addition was complete, the granules were allowed to air dry.

Then the separating layer was built up by spraying into the granulator an aqueous solution of the hydroxypropylmethylcellulose.

The enteric polymer was neutralized with ammonium hydroxide to dissolve it in water. A sufficient amount of water was used to prepare a 5% w/w solution, and sufficient ammonium hydroxide (28% ammonia solution) was added to achieve a pH of about 6.9. After the polymer had been neutralized, the triethyl citrate and talc were added to the solution, and gently stirred to suspend the talc. Then the suspension was applied to the subcoated granules in the granulator, using an inlet air temperature of about 70° C. After completing the enteric coating application, the pellets were placed onto a paper-lined tray and dried in the dryhouse at 110° F for 3 hours. The pellets were then filled into size #3 gelatin capsules.

EXAMPLE 6

10 mg Duloxetine base/capsule

| Bill of Materials | |
|---|---|
| Beads | |
| Sucrose—starch nonpareils, 20–25 mesh | 99.76 mg |
| Duloxetine layer | |
| Duloxetine | 11.23 |
| Hydroxypropylmethylcellulose | 4.50 |
| Separating layer | |
| Hydroxypropylmethylcellulose | 3.30 |
| Talc, 500 mesh | 7.60 |
| Enteric layer | |
| HPMCAS-LF | 16.11 |
| Triethyl citrate | 3.22 |
| Talc, 500 mesh | 12.26 |
| Finishing Layer | |
| Talc | Trace |
| | 157.98mg. |

The product was made in the same manner used in Example 5, except that the duloxetine suspension was passed through a Tri-Homo Disperser—Homogenizer (Tri-Homo Corporation, Salem, Mass., U.S.A.) mill. In order to alleviate static charge and to improve flow, a small amount of talc was added to the pellets prior to capsule filling.

EXAMPLE 7

| Bill of Materials | |
|---|---|
| Beads | |
| Sucrose—starch nonpareils 20–25 mesh | 109.86mg |
| Duloxetine layer | |
| Duloxetine | 11.23 |
| Hydroxypropylmethylcellulose | 4.48 |
| Separating layer | |
| Hydroxypropylmethylcellulose | 4.51 |

-continued

| Bill of Materials | |
|---|---|
| Enteric layer | |
| HPMCAS-LS | 24.34 |
| Talc, 500 mesh | 2.44 |
| Triethyl citrate | 7.31 |
| Polysorbate 80 | 0.25 |
| Emulsion silicone solids | 0.10 |
| Carboxymethylcellulose | 0.18 |
| Finishing layer | |
| Hydroxypropylmethylcellulose | 8.34 |
| Titanium dioxide | 2.78 |
| Propylene glycol | 3.70 |
| | 179.50 |

10 mg Duloxetine base/capsule

The duloxetine layer was built up by suspending duloxetine in a 4% w/w solution of the hydroxypropylmethylcellulose in water, and milling the suspension with a CoBall Mill (Fryma Mashinen AG, Rheinfelden, Switzerland) model MS-12. A fluid bed dryer with a Wurster column was used to make this product at a batch size of 1.0 kg. The separating layer was added from a 4% w/w solution of the hydroxypropylmethylcellulose in water.

In order to prepare the enteric coating suspension, purified water was cooled to 10° C. and the polysorbate, triethyl citrate and silicone emulsion were added and dispersed or dissolved. Then the HPMCAS and talc were added and agitated until homogeneity was obtained. To this suspension, a carboxymethylcellulose aqueous solution, 0.5% w/w, was added and blended thoroughly. The enteric suspension was maintained at 20° C. during the coating process. The enteric suspension was then added to the partially completed pellets in the Wurster column at a spray rate of about 15 ml/min, holding the temperature of the inlet air at about 50° C. The product was dried in the Wurster at 50° C. when the enteric suspension had been fully added, and then dried on trays for 3 hours in a dry house at 60° C. A finishing layer was then applied which consisted of a 4.5% w/w/ hydroxypropylmethylcellulose solution containing titanium dioxide and propylene glycol as plasticizer. The pellets were completely dried in the fluid bed dryer and then were then filled in size 3 gelatin capsules.

EXAMPLE 8

10 mg Duloxetine base/capsule

| Bill of Materials | |
|---|---|
| Beads | |
| Sucrose—starch nonpareils 20–25 mesh | 59.43mg. |
| Duloxetine layer | |
| Duloxetine | 11.23 |
| Hydroxypropylmethylcellulose | 4.50 |
| Emulsion silicone solids | 0.04 |
| Separating layer | |
| Hydroxypropylmethylcellulose | 2.26 |
| Talc, 500 mesh | 4.53 |
| Enteric layer | |
| HPMCAS-LS | 18.49 |

-continued

| Bill of Materials | |
|---|---|
| Talc, 500 mesh | 1.85 |
| Triethyl citrate | 5.55 |
| Polysorbate 80 | 0.19 |
| Emulsion silicone solids | 0.07 |
| Finishing layer | |
| Hydroxypropylmethylcellulose | 5.47 |
| Titanium dioxide | 1.82 |
| Propylene glycol | 2.43 |
| Talc | Trace |
| | 117.86 |

The product was made in essentially the same manner as that of Example 7 above, with the exception that approximately 25% of the enteric polymer had been neutralized with ammonium hydroxide prior to addition to the remaining components of the enteric coating suspension.

EXAMPLE 9

10 mg Duloxetine base/capsule

| Bill of Materials | |
|---|---|
| Beads | |
| Sucrose—starch nonpareils, 20–25 mesh | 60.33mg |
| Duloxetine layer | |
| Duloxetine | 11.22 |
| Hydroxypropylmethylcellulose | 3.75 |
| Separating layer | |
| Hydroxypropylmethylcellulose | 4.15 |
| Talc, 500 mesh | 12.46 |
| Enteric layer | |
| HPMCAS-LF | 24.82 |
| Triethyl citrate | 4.95 |
| Talc, 500 mesh | 7.45 |
| Finishing Layer | |
| Hydroxypropylmethylcellulose | 8.36 |
| Titanium dioxide | 2.79 |
| Talc | Trace |
| | 140.28mg |

The product was made essentially as was the product of Example 7. except that in this instance the HPMCAS-LF was fully neutralized to a pH of 5.7 and complete solubility in water.

EXAMPLE 10

10 mg Duloxetine base/capsule

| Bill of Materials | |
|---|---|
| Beads | |
| Sucrose - starch nonpareils, 20–25 mesh | 60.28mg |
| Duloxetine layer | |
| Duloxetine | 11.21 |
| Hydroxypropylmethylcellulose | 3.74 |

-continued

| Bill of Materials | |
|---|---|
| Separating layer | |
| Hydroxypropylmethylcellulose | 2.51 |
| Sucrose | 5.00 |
| Talc, 500 mesh | 10.03 |
| Enteric layer | |
| HPMCAS-LF | 25.05 |
| Triethyl citrate | 5.00 |
| Talc, 500 mesh | 7.52 |
| Finishing layer | |
| Hydroxypropylmethylcellulose | 8.44 |
| Titanium dioxide | 2.81 |
| Talc | Trace |
| | 141.60mg |

The product was made substantially according to the process used in Example 7. In this instance, the sucrose was dissolved in the water used to form the separating layer, and the HPMCAS-LF was fully neutralized.

EXAMPLE 11

10 mg Duloxetine base/capsule

| Bill of Materials | |
|---|---|
| Beads | |
| Sucrose—starch nonpareils, 20–25 mesh | 84.92mg |
| Duloxetine layer | |
| Duloxetine | 10.70 |
| Hydroxypropylmethylcellulose | 4.27 |
| Separating layer | |
| Hydroxypropylmethylcellulose | 2.22 |
| Sucrose | 6.68 |
| Talc, 500 mesh | 11.87 |
| Enteric layer | |
| HPMCAS-LF | 27.36 |
| Triethyl citrate | 5.47 |
| Talc, 500 mesh | 8.22 |
| Finishing layer | |
| Hydroxypropylmethylcellulose | 9.82 |
| Titanium dioxide | 2.55 |
| Yellow iron oxide | 0.72 |
| Talc | Trace |
| | 172.80mg |

The product was made substantially according to the process used in Example 10.

Pellets made according to the above examples, and gelatin capsules filled with various batches of such pellets, have been thoroughly tested in the manners usual in pharmaceutical science. Results of stability tests show that the pellets and capsules have sufficient storage stability to be distributed, marketed and used in the conventional pharmaceutical manner.

Testing further shows that the pellets and capsules pass the conventional tests for enteric protection under conditions prevailing in the stomach. It has also been shown that the pellets release their load of duloxetine acceptably quickly when exposed to conditions prevailing in the small intestine. Accordingly, the present invention has been demonstrated to solve the problems which previously were encountered in the formulation of other duloxetine pellets.

We claim:

1. An enteric duloxetine pellet comprising a) a core consisting of duloxetine and a pharmaceutically acceptable excipient; b) an optional separating layer; c) an enteric layer comprising hydroxypropylmethylcellulose acetate succinate (HPMCAS) and a pharmaceutically acceptable excipient; d) an optional finishing layer.

2. A pellet of claim 1 wherein the HPMCAS is partially neutralized with ammonium ions to the degree that from about 0% to about 25% of the succinic acid groups are neutralized.

3. A pellet of claim 2 wherein the HPMCAS is partially neutralized to the degree that from about 0% to about 15% of the succinic acid groups are neutralized.

4. A pellet of claim 1 wherein the separating layer is present.

5. A pellet of claim 1 wherein the average particle size of the duloxetine is about 50 μm or less.

6. A pellet of claim 5 wherein the core comprises an inert bead on which the duloxetine is deposited as a layer comprising in addition a pharmaceutically acceptable excipient.

7. A pellet of claim 6 wherein the separating layer is present.

8. A pellet of claim 7 wherein the HPMCAS is partially neutralized with ammonium ions to the degree that from about 0% to about 25% of the succinic acid groups are neutralized.

9. A pellet of claim 4 wherein the separating layer comprises a pharmaceutically acceptable sugar.

10. A pellet of claim 9 wherein the sugar is sucrose.

11. A process for preparing an enteric duloxetine pellet comprising a) providing a core consisting of duloxetine and a pharmaceutically acceptable excipient; b) optionally, applying to the core a separating layer comprising a pharmaceutically acceptable excipient; c) applying an enteric layer comprising HPMCAS and a pharmaceutically acceptable excipient, wherein the HPMCAS is supplied as an aqueous solution or suspension and the application takes place in an apparatus of the fluid bed type; d) optionally, applying a finishing layer.

12. A process of claim 11 wherein the HPMCAS is fully or partially neutralized with ammonium ions.

13. A process of claim 12 wherein the HPMCAS is neutralized to the degree that from about 25% to about 100% of the succinic acid groups are neutralized.

14. A process of claim 11 wherein the separating layer is applied.

15. A process of claim 14 wherein the separating layer comprises a pharmaceutically acceptable sugar.

16. A process of claim 15 wherein the sugar is sucrose.

17. A process of claim 11 wherein the core is prepared by applying duloxetine and a pharmaceutically acceptable excipient to an inert bead.

18. A process of claim 17 wherein the separating layer is applied and comprises a pharmaceutically acceptable sugar.

* * * * *